United States Patent
Ying et al.

(10) Patent No.: US 9,884,888 B2
(45) Date of Patent: Feb. 6, 2018

(54) CHEMICAL REGENERATION METHOD OF OXIDIZED COENZYME NAD (P)+

(71) Applicant: NANJING TECH UNIVERSITY (CN), Nanjing (CN)

(72) Inventors: Hanjie Ying, Nanjing (CN); Chenjie Zhu, Nanjing (CN); Qing Li, Nanjing (CN); Zhuotao Tan, Nanjing (CN); Lingling Pu, Nanjing (CN)

(73) Assignee: NANJING TECH UNIVERSITY, Nanjing (CN)

( * ) Notice: Subject to any disclaimer, the term of this patent is extended or adjusted under 35 U.S.C. 154(b) by 0 days.

(21) Appl. No.: 15/159,029

(22) Filed: May 19, 2016

(65) Prior Publication Data

US 2017/0114085 A1  Apr. 27, 2017

(51) Int. Cl.
C07H 19/207 (2006.01)
C12P 19/36 (2006.01)

(52) U.S. Cl.
CPC ............ *C07H 19/207* (2013.01); *C12P 19/36* (2013.01); *Y02P 20/584* (2015.11)

(58) Field of Classification Search
None
See application file for complete search history.

(56) References Cited

FOREIGN PATENT DOCUMENTS

| CN | 105483167 A | * | 4/2016 | |
| EP | 2333101 A1 | * | 6/2011 | ........... C12N 9/0036 |

OTHER PUBLICATIONS

Zhu et al. "Nonenzymatic and Metal-Free Organocatalysis for in Situ Regeneration of Oxidized Cofactors by Activation and Reduction of Molecular Oxygen." ACS Catalysis 6(8): 4989-4994, Jun. 30, 2016 (Year: 2016).*
Min et al. (CN 105483167 A) EPO machine translation (Year: 2016).*
Pharmazell GMBH (EP2333101 A1) EPO machine translation (Year: 2011).*
Cheikhou et al. "Electrochemical microreactor for chiral syntheses using the cofactor NADH." AIChE journal 54(5): 1365-1376, 2008 (Year: 2008).*
Hollmann et al. "Stereospecific biocatalytic epoxidation: the first example of direct regeneration of a FAD-dependent monooxygenase for catalysis", Journal of the American Chemical Society 125 (27): 8209-8217, 2003 (Year: 2003).*
Murray et al. "Biomimetic flavin-catalyzed aldehyde oxidation", Organic Letters 14 (14): 3656-3659, 2012 (Year: 2012).*
Marsh et al. "Chemoselective sulfide oxidation mediated by bridged flavinium organocatalysts." Tetrahedron Letters 51(17): 2362-2365, 2010 (Year: 2010).*

* cited by examiner

*Primary Examiner* — Emily A Cordas
(74) *Attorney, Agent, or Firm* — CBM Patent Consulting, LLC

(57) ABSTRACT

It discloses a chemical regeneration method of oxidized coenzyme $NAD(P)^+$ which is under an oxygen or air atmosphere condition, adding a catalytic amount of bridged flavin, and oxidizing $NAD(P)H$ to obtain $NAD(P)^+$. The catalyst for regeneration of cofactor is cheap and easily available small organic molecule having no noble metal; this regeneration system can regenerate NADH and NADPH; this regeneration system has a wide pH range and temperature range, being applicable to various oxidation reactions catalyzed by nicotinamide-dependent oxidoreductase.

17 Claims, 2 Drawing Sheets

CHEMICAL REGENERATION METHOD OF OXIDIZED COENZYME NAD (P)+

The application is related to Chinese application Ser. No. CN201610013723.4, filed on Jan. 8, 2016 and entitled "CHEMICAL REGENERATION METHOD OF OXIDIZED COENZYME NAD(P)+", which is hereby incorporated herein by reference.

TECHNICAL FIELD

The present invention relate to a chemical regeneration method of oxidized coenzyme NAD(P)$^+$, it belongs to a technical field of coenzyme regeneration.

BACKGROUND OF THE INVENTION

Oxidoreductase is a kind of enzyme being most widely used after hydrolase, most of the oxidation-reduction reactions catalyzed by it needs NAD(P)H/NAD(P)$^+$ to provide reduced hydrogen or to receive hydrogen, but high price of NAD(P)H/NAD(P)$^+$ restricts use of the oxidoreductase in industrial production, requiring conducting in situ regeneration of coenzyme to reduce the cost. At present, the coenzyme regeneration includes five methods of whole-cell method, enzyme method, electrochemical method, photochemical method and chemical method. For the whole-cell method, its cost is low, but product separation is complicated, the method is comparatively primitive. The enzyme method includes two methods of substrate coupling method and enzyme coupling method, wherein the substrate coupling method is the same enzyme catalyze both of two different substrates towards reverse directions, meanwhile achieving conversion of main substrate and co-substrate, forming a coenzyme regeneration circulation, co-substrate and main substrate compete an active center of the enzyme, a part of the enzyme activity is used in regeneration of coenzyme, thus the enzyme activity used in catalyzing the main substrate is reduced; in the enzyme coupling method, the oxidization reaction enzyme system and the reduction reaction enzyme system works in one system in parallel, production of the enzyme catalyzes substrate conversion and consumes coenzyme, regeneration of the enzyme catalyzes regeneration of the coenzyme, this method requires that the substrates in two enzyme systems must be independent to each other, to avoid mutual competition to active center of the same enzyme, and optimum reaction condition for these two enzymes are often inconsistent. For the eletrochemical method, the cost of electricity is low, there is no stoichiometric regeneration reagent, but the efficiency is low, often requiring participation of a medium, and this method is incompatible to many biochemical catalytic systems, its selectivity is poor. The chemical method uses a special catalyst to transfer oxid-reduction equivalent of the oxidant and reductant to a redox cofactor NAD(P)H/NAD(P)$^+$ thereby forming a cofactor regeneration circulation, the commonly used chemical catalyst is a noble metal organic complex (Rh/Ru/Ir), its price is high and center metal may fall off, the center metal often coordinates with amino acid residue of the enzyme, making the metal catalyst and the enzyme both losing activity. The photochemical regeneration method is often limited by deficiency of efficient photosensitizer, thus generally its efficiency is low.

The chemical method currently used in regeneration of the oxidized cofactor NAD(P)$^+$ often uses two kinds of regeneration catalyst for riboflavin mononucleotide (FMN) [*J. Am. Chem. Soc.* 1982, 104, 4659-4665] and iron (III) porphyrin [*Angew. Chem. Int. Ed.* 2011, 50, 2397-2400]. When the FMN is used in the regeneration, it is required to use overdose [*J. Am. Chem. Soc.* 1982, 104, 4659-4665] or under radiation of a special light source [*Chem Cat Chem* 2011, 3, 338-342] to conduct catalytic regeneration. The iron porphyrin belongs to metal organic complex, its regeneration efficiency is not high, and tends to coordinate with the enzyme, resulting in deactivation.

SUMMARY OF THE INVENTION

In consideration of above-described problems, the technical problem to be resolved by the present invention is to provide a new chemical method which uses bridged flavin regeneration NAD(P)+, to overcome the shortcomings of other regeneration methods.

To resolve the above-described technical problem, the technical solution adopted by the present invention is as follows:

The first technical solution to be protected by the present invention is a chemical regeneration method of oxidized coenzyme NAD(P)$^+$.

A chemical regeneration method of oxidized coenzyme NAD(P)$^+$, the method is under oxygen or air atmosphere condition, adding a catalytic amount of bridged flavin, oxidizing NAD(P)H to obtain NAD(P)$^+$.

The NAD(P)$^+$ of the present invention is NAD$^+$ or NADP$^+$.

The NAD(P)H of the present invention is NADH or NADPH.

Wherein, NADH is oxidized to obtain NAD$^+$, and NADPH is oxidized to obtain NADP$^+$.

For the bridged flavin (English name N$^1$,N$^{10}$-ethylene-bridged flavins) of the present invention, its general structure formula is as follow:

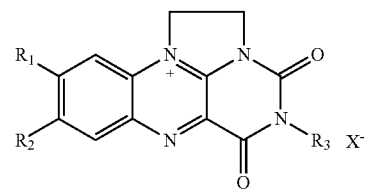

wherein, R$_1$ and R$_2$ are independently selected from hydrogen, methyl, trifluoromethyl, methoxyl, halogen atom, nitro, amino; R$_3$ is selected from hydrogen, C1-C5 alkyl, phenyl, benzyl; X$^-$ is selected from halide ion, nitrate radical, trifluorommethanesulfonic acid radical.

It is preferred that, R$_1$ includes but not limited to hydrogen, methyl, halogen atom; R$_2$ includes but not limited to hydrogen, methyl, halogen atom, trifluoromethyl; R$_3$ includes but not limited to hydrogen, methyl; X$^-$ is a halide ion.

It is most preferred that, the bridged flavin includes but not limited to 7-trifluoromethyl-1,10-ethyleneisoalloxazine chloride (Compound I), 8-chloro-1,10-ethyleneisoalloxazine chloride (Compound II), or 1,10-ethyleneisoalloxazine chloride (Compound III).

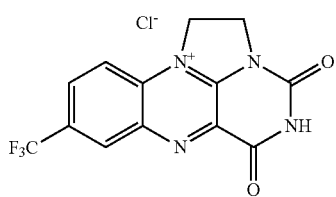

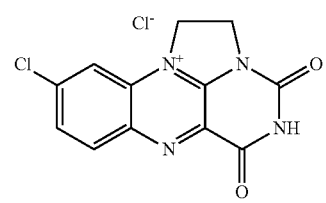

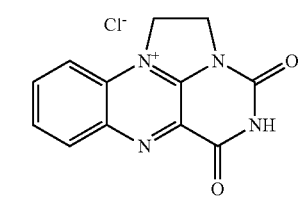

The bridged flavin of the present invention can be synthesized by referring to existing disclosed literatures, e.g., Literature [*Tetrahedron*, 2001, 57, 4507-4522]; or directly purchased from the market.

Wherein, the mole percentage of the catalytic amount of the bridged flavin is 0.1-5%, preferably 0.25-2%, most preferably 2% of NAD(P)H.

Wherein, the condition for oxidizing NAD(P)H to obtain NAD(P)$^+$ is pH 4-10, temperature 30-70° C.; preferably the condition for oxidizing NAD(P)H to obtain NAD(P)$^+$ is pH 6-8 and temperature 30-40° C.; most preferably the condition for oxidizing NAD(P)H to obtain NAD(P)$^+$ is pH 7 and temperature 30° C.

Wherein, the reaction time for oxidizing NAD(P)H to obtain NAD(P)$^+$ is generally based on the reaction being complete or most of the reaction being complete, a person skilled in the art can adopt a ultraviolet spectrophotometry to detect the completion of reaction, because NAD(P)H has a ultraviolet absorption at 340 nm, but NAD(P)$^+$ has no absorption at 340 nm, thus the ultraviolet spectrophotometry can be used to detect reaction process, when the sample absorbance after subtracting by blank absorbance of the flavin is reduced to 0, it is regarded that the reaction is complete, when the absorbance approaches 0, it is regarded that most of the reaction is complete, of course a person skilled in the art can also use other existing detecting methods to monitor the reaction progress such that the reaction is complete.

Wherein, the bridged flavin, as a NAD(P)$^+$ regeneration catalyst, can be coupled with the oxidation reaction catalyzed by NAD(P)$^+$-dependent oxidoreductase, forming a regeneration circulation system of coenzyme NAD(P)$^+$.

Wherein, the NAD(P)$^+$-dependent oxidoreductase includes but not limited to all enzymes of EC1.1.1.X, EC1.2.1.X, EC1.3.1.X, EC1.4.1.X, EC1.5.1.X, EC1.6.1.X, EC1.7.1.X, EC1.8.1.X, EC1.10.1.X, EC1.12.1.X, EC1.13.1.X, EC1.16.1.X, EC1.17.1.X, EC1.18.1.X, EC1.20.1.X, EC1.22.1.X. It is preferred that, the NAD(P)$^+$-dependent oxidoreductase includes but not limited to horse liver alcohol dehydrogenase, glucose dehydrogenase or glycerol dehydrogenase.

When the bridged flavin, as NAD(P)$^+$ regeneration catalyst, is coupled with the oxidation reaction catalyzed by NAD(P)$^+$-dependent oxidoreductase, the amount of the bridged flavin is 0.1-5%, preferably 0.25-2%, most preferably 2% of mole number of the substrate catalyzed by NAD(P)$^+$-dependent oxidoreductase.

The second technical solution to be protected by the present invention is an oxidation reaction.

A oxidation reaction, it uses NAD(P)$^+$-dependent oxidoreductase as a catalyst, and the bridged flavin as the NAD(P)$^+$ regeneration catalyst, under an oxygen or air atmosphere condition, oxidizing NAD(P)H to obtain NAD(P)$^+$, forming a regeneration circulation system of the coenzyme NAD(P)$^+$.

The NAD(P)$^+$ of the present invention is NAD$^+$ or NADP$^+$.

The NAD(P)H of the present invention is NADH or NADPH.

Wherein, NADH is oxidized to obtain NAD$^+$, and NADPH is oxidized to obtain NADP$^+$.

For the bridged flavin of the present invention (English name N$^1$,N$^{10}$-Ethylene-bridged flavins), its general structure formula is as follow:

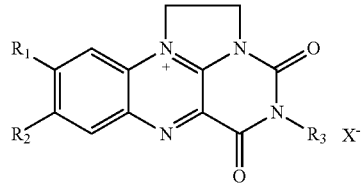

wherein, R$_1$ and R$_2$ are independently selected from hydrogen, methyl, trifluoromethyl, methoxyl, halogen atom, nitro, amino; R$_3$ is selected from hydrogen, C1-C5 alkyl, phenyl, benzyl; X$^-$ is selected from halide ion, nitrate radical, trifluoromethanesulfonic acid radical.

It is preferred that, R$_1$ includes but not limited to hydrogen, methyl, halogen atom; R$_2$ includes but not limited to hydrogen, methyl, halogen atom, trifluoromethyl; R$_3$ includes but not limited to hydrogen, methyl; X$^-$ is halide ion.

It is most preferred that, the bridged flavin includes but not limited to 7-trifluoromethyl-1,10-ethyleneisoalloxazine chloride (Compound I), 8-chloro-1,10-ethyleneisoalloxazine chloride (Compound II), or 1,10-ethyleneisoalloxazine chloride (Compound III).

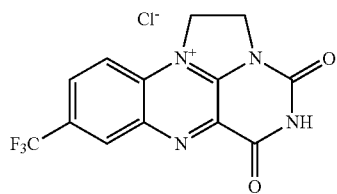

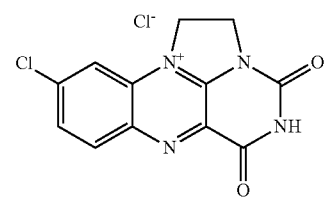

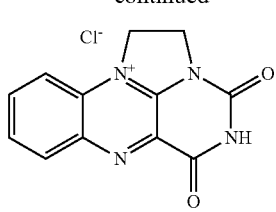

The bridged flavin of the present invention can be synthesized by referring to existing disclosed literatures, e.g., Literature [*Tetrahedron*, 2001, 57, 4507-4522]; or directly purchased from the market.

Wherein, mole number catalyzed by the bridged flavin is 0.1-5%, preferably 0.25-2%, most preferably 2% of mole number of the substrate catalyzed by NAD(P)$^+$-dependent oxidoreductase.

Wherein, the condition for oxidizing NAD(P)H to obtain NAD(P)$^+$ is PH 3-12 and temperature 30-70° C.; preferably the condition for oxidizing NAD(P)H to obtain NAD(P)$^+$ is pH 6-8 and temperature 30-40° C.; most preferably the condition for oxidizing NAD(P)H to obtain NAD(P)$^+$ is pH 7 and temperature 30° C.

Wherein, the NAD(P)$^+$-dependent oxidoreductase includes but not limited to all enzymes of EC1.1.1.X, EC1.2.1.X, EC1.3.1.X, EC1.4.1.X, EC1.5.1.X, EC1.6.1.X, EC1.7.1.X, EC1.8.1.X, EC1.10.1.X, EC1.12.1.X, EC1.13.1.X, EC1.16.1.X, EC1.17.1.X, EC1.18.1.X, EC1.20.1.X, EC1.22.1.X. It is preferred that, the NAD(P)$^+$-dependent oxidoreductase includes but not limited to horse liver alcohol dehydrogenase, glucose dehydrogenaseor glycerol dehydrogenase.

The third technical solution to be protected by the present invention is use of bridged flavin as a catalyst in oxidizing NAD(P)H to obtain NAD(P)$^+$.

The NAD(P)$^+$ of the present invention is NAD$^+$ or NADP$^+$.

The NAD(P)H of the present invention is NADH or NADPH.

Wherein, NADH is oxidized to obtain NAD$^+$, and NADPH is oxidized to obtain NADP$^+$.

For the bridged flavin of the present invention (English name N$^1$,N$^{10}$-Ethylene-bridged flavins), its general structure formula is as follow:

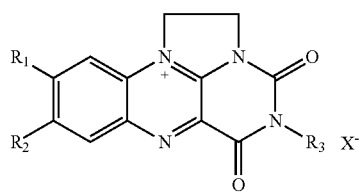

wherein, R$_1$ and R$_2$ are independently selected from hydrogen, methyl, trifluoromethyl, methoxyl, halogen atom, nitro, amino; R$_3$ is selected from hydrogen, C1-C5 alkyl, phenyl, benzyl; X$^-$ is selected from halide ion, nitrate radical, trifluoromethanesulfonic acid radical.

It is preferred that, R$_1$ includes but not limited to hydrogen, methyl, halogen atom; R$_2$ includes but not limited to hydrogen, methyl, halogen atom, trifluoromethyl; R$_3$ includes but not limited to hydrogen, methyl; X$^-$ is halide ion.

It is most preferred that, the bridged flavin includes but not limited to 7-trifluoromethyl-1,10-ethyleneisoalloxazine chloride (Compound I), 8-chloro-1,10-ethyleneisoalloxazine chloride (Compound II), or 1,10-ethyleneisoalloxazine chloride (Compound III).

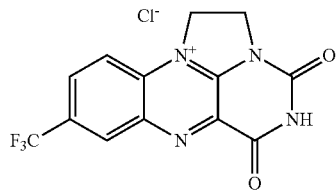

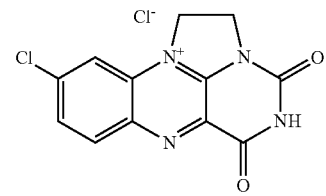

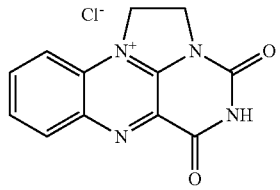

The bridged flavin of the present invention can be synthesized by referring to existing disclosed literatures, e.g. Literature [*Tetrahedron*, 2001, 57, 4507-4522]; or directly purchased from the market.

Wherein, the mole number catalyzed by the bridged flavin is 0.1-5%, preferably 0.25-2%, most preferably 2% of mole number of NAD(P)H.

Wherein, the condition for oxidizing NAD(P) H to obtain NAD(P)$^+$ is pH 4-10 and temperature 30-70° C.; preferably the condition for oxidizing NAD(P)H to obtain NAD(P)$^+$ is pH 6-8 and temperature 30-40° C.; most preferably the condition for oxidizing NAD(P)H to obtain NAD(P)$^+$ is pH 7 and temperature 30° C.

Wherein, the reaction time for oxidizing NAD(P)H to obtain NAD(P)$^+$ is generally based on the react being complete or most the reaction being complete, a person skilled in the art cat uses ultraviolet spectrophotometry to detect completion of the reaction, because NAD(P)H has an ultraviolet absorption at 340 nm, but NAD(P)$^+$ has no absorption at 340 nm, thus ultraviolet spectrophotometry can be used to detect the reaction process, when the absorbance of the sample after subtracting by blank absorbance of the bridged flavin is reduced to 0, it is regarded that the reaction is complete, when absorbance is close to 0, it is regarded that most of the reaction is complete, of course, a person skilled in the art can also adopt other existing detecting method to monitor the reaction process such that the reaction is complete.

Beneficial effect: Compared to the prior art, the main advantage of the present invention is: the efficiency of regenerating NAD(P)$^+$ by the bridged flavin is very high, the TOF can be up to 19 min$^{-1}$, and it can completely converting, application extent is wide, the condition is pH 4-10 and temperature 30-70° C. It can be coupled with various

DESCRIPTION OF THE EMBODIMENTS

Figure 1:
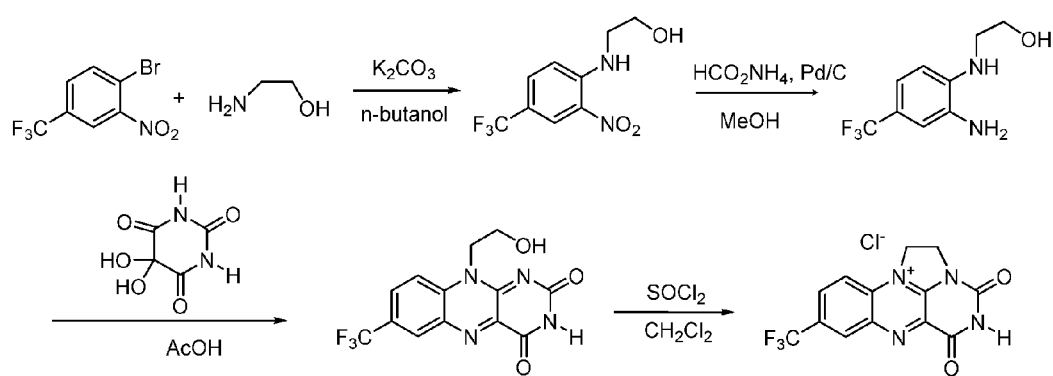
FIG. 1 is a synthesis route diagram of 7-trifluoromethyl-1,10-ethyleneisoalloxazine chloride.
Figure 2:
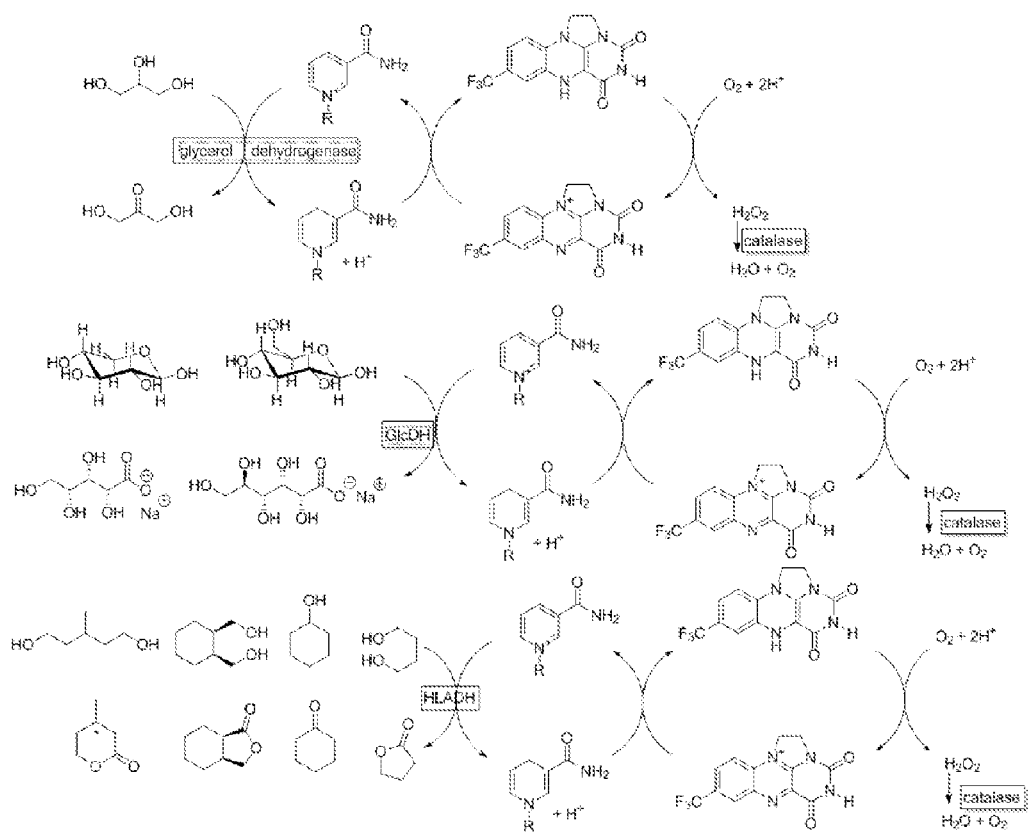
FIG. 2 is a route diagram of a coupling reaction of 7-trifluoromethyl-1,10-ethyleneisoalloxazine chloride as a $NAD^+$ regeneration catalyst with horse liver alcohol dehydrogenase and glucose dehydrogenase.

Based on the following examples, the present invention can be better understood. However, a person skilled in the art will readily understand that, the contents described in the examples are only used to illustrate the present invention, and should not and will not restrict the present invention described in detail in the claims.

Example 1: Synthesis of 7-Trifluoromethyl-1,10-Ethyleneisoalloxazine Chloride 4-bromo-3-nitrotrifluorotoluene (1.76 g, 6.53 mmol) and ethanolamine (1.19 g, 19.59 mmol) were dissolved in 20 mL ethanol, potassium carbonate (1.08 g, 7.83 mmol) was added and stirred under reflux for 5-6 hours, after the reaction solution was cooled, filtered, the filtrate was concentrated under reduced pressure, to obtain an orange solid, and 20 mL saturated brine was added, extracted with ethyl acetate (3×40 mL), the organic phases were combined, washed with a saturated brine, dried on anhydrous sodium sulfate, rotary evaporated, purified by silica gel column chromatography to obtain 4-trifluoromethyl-2-nitro-N-(2-hydroxyethyl)aniline (1.58 g, yield 96%).

To an anhydrous methanol solution of 4-trifluoromethyl-2-nitro-N-(2-hydroxyethyl)aniline (1.20 g, 4.80 mmol) (5° C.), ammonium formate (1.51 g, 24.0 mmol) and 5% Pd/C (1.60 g) were added, stirred and reacted at 0 to 25° C. for 1 hour, filtered, the filter residue was washed with methanol, the filtrate was concentrated under reduced pressure, producing a red solid, 30 mL saturated brine was added, extracted with ethyl acetate (3×30 mL), the organic phases were combined, dried on anhydrous sodium sulfate, filtered, concentrated under reduced pressure, to obtain a white solid (1.04 g, 94%).

To a 50° C. acetic acid solution of 4-trifluoromethyl-N-(2-hydroxyethyl)-o-phenylenediamine (1 g, 4.35 mmol) filled with argon, alloxan monohydrate (0.73 g, 4.35 mmol) and boric acid (0.29 g, 4.67 mmol) were added, reacted for 1 hour, cooled, the obtained yellow solid was filtered, washed with dichloromethane, vacuum dried, the obtained yellow solid was immediately placed into a round bottom flask filled with nitrogen gas, and thionyl chloride (20 mL) was slowly added meanwhile vigorously stirred, reacted for 16 hours under 50° C. nitrogen gas shielding, then cooled and filtered, the obtained solid was washed with dichloromethane, the crude product was dissolved in a minimal amount of 98% formic acid solution, and recrystallized with diethyl ether, to obtain a yellow solid (1.28 g, 95%). ESI-MS$^+$: 309; $^1$H NMR (CD$_3$COOD-CF$_3$COOH, 1:6) δ 4.96 (t, J=8.9 Hz, 2H), 5.58 (t, J=8.9 Hz, 2H), 8.20 (d, J=8.8 Hz, 1H), 8.47 (d, J=8.8 Hz, 1H), 8.81 (s, 1H), $^{13}$C NMR (CD3COOD-CF$_3$COOH, 1:6) δ 46.2, 52.1, 122.6 (q, J=272.6 Hz, CF$_3$), 118.9, 131.4, 131.7, 133.9, 135.4 (q, J=35.5 Hz, C CF$_3$), 136.8, 141.1, 145.2, 146.4, 158.8.

Example 2: Synthesis of 1,10-Ethyleneisoalloxazine Chloride 2-fluoronitrobenzene (0.92 g, 6.53 mmol) and ethanolamine (1.19 g, 19.59 mmol) were dissolved in 20 mL ethanol, potassium carbonate (1.08 g, 7.83 mmol) was added and stirred under reflux for 5-6 hours, after the reaction solution was cooled, filtered, the filtrate was concentrated under reduced pressure, to obtain an orange solid, and 20 mL saturated brine was added, extracted with ethyl acetate (3×40 mL), the organic phases were combined, washed with a saturated brine, dried on anhydrous sodium sulfate, rotary evaporated, purified by silica gel column chromatography to obtain 2-nitro-N-(2-hydroxyethyl)aniline (0.98 g, yield 82.9%).

To a anhydrous methanol solution (5° C.) of 2-nitro-N-(2-hydroxyethyl)aniline (0.87 g, 4.80 mmol), ammonium formate (1.51 g, 24.0 mmol) and 5% Pd/C (1.60 g) were added, stirred and reacted at 0-25° C. for 1 hour, filtered, the filter residue was washed with methanol, the filtrate was concentrated under reduced pressure, producing a red solid, and 30 mL saturated brine was added, extracted with ethyl acetate (3×30 mL), the organic phases were combined, dried on anhydrous sodium sulfate, filtered, concentrated under reduced pressure, to obtain a white solid (0.67 g, 92%).

In a 50° C. acetic acid solution of N-(2-hydroxyethyl)-o-phenylenediamine (0.66 g, 4.35 mmol) filled with argon, alloxan monohydrate (0.73 g, 4.35 mmol) and boric acid (0.29 g, 4.67 mmol) were added, reacted for 1 hour, cooled, the resulting yellow solid was filtered, washed with dichloromethane, vacuum dried, the yellow solid obtained was immediately placed into a round bottom flask filled with nitrogen gas, and thionyl chloride (20 mL) was slowly added meanwhile vigorously stirred, reacted for 16 hours under 50° C. nitrogen gas shielding, then cooled and filtered, the solid obtained was washed with dichloromethane, the crude product was dissolved in a minimal amount of 98% formic acid solution, and recrystallized with diethyl ether, to obtain a yellow solid (0.88 g, 73%). ESI-MS+: 240.8, $^1$H NMR (CD3COOD-CF$_3$COOH, 1:6) δ 4.94 (t, J=8.9 Hz, 2H), 5.53 (t, J=8.9 Hz, 2H), 8.04-8.57 (4H); $^{13}$C NMR (CD3COOD-CF$_3$COOH, 1:6) δ 45.9, 51.9, 117.2, 130.3, 131.9, 133.2, 134.2, 142.1, 142.2, 144.1, 146.7, 159.4.

Example 3: Synthesis of 8-Chloro-1,10-Ethyleneisoalloxazine Chloride 2,4-dichloronitrobenzene (1.25 g, 6.53 mmol) and ethanolamine (1.19 g, 19.59 mmol) were dissolved in 20 mL ethanol, potassium carbonate (1.08 g, 7.83 mmol) was added and stirred under reflux for 5-6 hours, after the reaction solution was cooled, filtered, the filtrate was concentrated under reduced pressure, to obtain an orange solid, and 20 mL saturated brine was added, extracted with ethyl acetate (3×40 mL), the organic phases were combined, washed with saturated brine, dried on anhydrous sodium sulfate, rotary evaporated, purified by silica gel column chromatography to obtain 5-chloro-2-nitro-N-(2-hydroxyethyl)aniline (1.26 g, yield 89%).

To a 20 mL water solution (100° C.) containing 5-chloro-2-nitro-N-(2-hydroxyethyl)aniline (1.04 g, 4.80 mmol) and Sn (1.71 g, 14.40 mmol), 9 mL concentrated hydrochloric acid was slowly dripped in, then the reaction was placed at 5° C. and cooled for 30 minutes, neutralized with a 50%

NaOH water solution, extracted with ethyl acetate (3×30 mL), the organic phases were combined, dried on anhydrous sodium sulfate, filtered, concentrated under reduced pressure, to obtain a white solid (0.47 g, 52%).

To a 50° C. acetic acid solution of 4-trifluoromethyl-N-(2-hydroxyethyl)-o-phenylenediamine (0.37 g, 2.0 mmol) filled with argon, alloxan monohydrate (0.32 g, 2.0 mmol) and boric acid (0.13 g, 2.14 mmol) were added, and reacted for 1 hour, cooled, the solid formed was filtered, washed with dichloromethane, vacuum dried, the solid obtained was immediately placed into a round bottom flask filled with nitrogen gas, and thionyl chloride (10 mL) was slowly added meanwhile stirred vigorously, reacted for 16 hours under 50° C. nitrogen gas shielding, then cooled and filtered, the solid obtained was washed with dichloromethane, the crude product was dissolved in a minimal amount of 98% formic acid solution, and recrystallized with diethyl ether, to obtain a solid (0.43 g, 69%). ESI-MS+: 274.9, $^1$H NMR (CD3COOD-CF$_3$COOH, 1:6) δ 4.92 (t, J=8.9 Hz, 2H), 5.49 (t, J=8.9 Hz, 2H), 8.06 (d, J=8.4 Hz, 2H), 8.50 (d, J=8.4 Hz, 1H); $^{13}$C NMR (CD3COOD-CF$_3$COOH, 1:6) δ 45.9, 51.9, 117.2, 130.9, 131.8, 134.2, 135.1, 140.6, 144.6, 146.6, 150.1, 159.1.

Example 4: 7-Trifluoromethyl-1,10-Ethyleneisoalloxazine Chloride Oxidizing NADH to NAD$^+$ At 30° C., in a 10 mL 50 mM potassium phosphate buffer of pH 7, the initial concentration of NADH was 0.2 mM, the concentration of 7-trifluoromethyl 1,10-ethyleneisoalloxazine chloride was 4 μM, the reaction solution was connected with the outside air. The change of the light absorption value of the reaction system at 340 nm was detected every 2 minutes, the conversion rate was calculated, and the results were shown in Table 1.

TABLE 1

Conversion rate of 7-trifluoromethyl-1,10-ethyleneisoalloxazine chloride oxidizing NADH with time

| time (min) | light absorption value at 340 nm | conversion rate (%) |
|---|---|---|
| 0 | 1.244 | 0.00 |
| 1 | 0.5991 | 51.84 |
| 2 | 0.2815 | 77.37 |
| 3 | 0.1425 | 88.55 |
| 4 | 0.0676 | 94.57 |
| 5 | 0.0313 | 97.48 |
| 6 | 0.0137 | 98.90 |
| 7 | 0.0056 | 99.55 |
| 8 | 0.002 | 99.84 |
| 9 | 0 | 100 |

Example 5: 7-Trifluoromethyl-1,10-Ethyleneisoalloxazine Chloride Oxidizing NADPH to NADP$^+$ At 30° C., in a 10 mL 50 mM potassium phosphate buffer of pH 7, the initial concentration of NADPH was 0.2 mM, the concentration of 7-trifluoromethyl 1,10-ethyleneisoalloxazine chloride was 4 μM, the reaction solution was connected with the outside air. Change of light absorption value of the reaction system at 340 nm was detected every 2 minutes, the conversion rate was calculated, and the results are shown in Table 2.

TABLE 2

Conversion rate of 7-trifluoromethyl-1,10-ethyleneisoalloxazine chloride oxidizing NADPH with time

| time (min) | light absorption value at 340 nm | conversion rate (%) |
|---|---|---|
| 0 | 1.244 | 0.00 |
| 1 | 0.5862 | 52.88 |
| 2 | 0.204 | 83.60 |
| 3 | 0.0983 | 92.10 |
| 4 | 0.0215 | 98.27 |
| 5 | 0.0098 | 99.21 |
| 6 | 0.0033 | 99.73 |
| 7 | 0 | 100 |

Example 6: 8-Chloro-1,10-Ethyleneisoalloxazine Chloride Oxidizing NADH to NAD$^+$ At 30° C., in a 10 mL 50 mM potassium phosphate buffer of pH 7, the initial concentration of NADH was 0.2 mM, the concentration of 8-chloro-1,10-ethyleneisoalloxazine chloride was 4 μM, the reaction solution was connected with the outside air. Change of the light absorption value of the reaction system at 340 nm was detected every 2 minutes, the conversion rate of NADH was calculated, and the results are shown in Table 3.

TABLE 3

Conversion rate of 8-chloro-1,10-ethyleneisoalloxazine chloride oxidizing NADH with time

| time (min) | light absorption value | conversion rate (%) |
|---|---|---|
| 0 | 1.244 | 0.00 |
| 1 | 0.721 | 42.04 |
| 2 | 0.5612 | 54.89 |
| 3 | 0.4401 | 64.62 |
| 4 | 0.3471 | 72.10 |
| 5 | 0.2751 | 77.89 |
| 6 | 0.2192 | 82.38 |
| 7 | 0.1752 | 85.92 |
| 8 | 0.1406 | 88.70 |
| 9 | 0.1133 | 90.89 |
| 10 | 0.092 | 92.60 |
| 11 | 0.0751 | 93.96 |
| 12 | 0.0615 | 95.06 |
| 13 | 0.0506 | 95.93 |
| 14 | 0.042 | 96.62 |
| 15 | 0.0352 | 97.17 |
| 16 | 0.0299 | 97.60 |
| 17 | 0.0255 | 97.95 |
| 18 | 0.0219 | 98.24 |
| 19 | 0.0192 | 98.46 |
| 20 | 0.0169 | 98.64 |

Example 7: 1,10-Ethyleneisoalloxazine Chloride Oxidizing NADH to NAD$^+$

At 30° C., in a 10 mL 50 mM potassium phosphate buffer of pH 7, the initial concentration of NADH was 0.2 mM, the concentration of 1,10-ethyleneisoalloxazine chloride was 4 μM, the reaction solution was connected with the outside air. Change of the light absorption value of the reaction system at 340 nm was detected every 2 minutes, the conversion rate of NADH was calculated, and the results are shown in Table 4.

TABLE 4

Conversion rate with time of 1,10-ethyleneisoalloxazine chloride oxidizing NADH

| time (min) | light absorption value | conversion rate (%) |
|---|---|---|
| 0 | 1.244 | 0.00 |
| 1 | 0.7525 | 39.51 |
| 2 | 0.616 | 50.48 |
| 3 | 0.5059 | 59.33 |
| 4 | 0.4166 | 66.51 |
| 5 | 0.3436 | 72.38 |
| 6 | 0.2839 | 77.18 |
| 7 | 0.2354 | 81.08 |
| 8 | 0.1957 | 84.27 |
| 9 | 0.163 | 86.90 |
| 10 | 0.1363 | 89.04 |
| 11 | 0.1145 | 90.80 |
| 12 | 0.0964 | 92.25 |
| 13 | 0.0816 | 93.44 |
| 14 | 0.0693 | 94.43 |
| 15 | 0.0591 | 95.25 |
| 16 | 0.0506 | 95.93 |
| 17 | 0.0436 | 96.50 |
| 18 | 0.038 | 96.95 |
| 19 | 0.0334 | 97.32 |
| 20 | 0.0295 | 97.63 |

Example 8: 7-Trifluoromethyl-1,10-Ethyleneisoalloxazine Chloride Oxidizing NADH at Different pHs At 30° C., respectively in 10 mL 50 mM potassium phosphate buffer of pH 4-10, the initial concentration of NADH was 0.2 mM, the concentration of 7-trifluoromethyl 1,10-ethyleneisoalloxazine chloride being added was 0.5 µM, the reaction solution was connected with the outside air, after being reacted for 10 minutes, the light absorption value at 340 nm was detected, the concentrations of NADH and NAD$^+$ were calculated, TON and TOF at different pHs were calculated, and the results are shown in Table 5, when pH<7, TON and TOF were increased with increase in pH, when pH>7, TON and TOF were reduced with increase in pH.

TABLE 5

TON and TOF of 7-trifluoromethyl-1,10-ethyleneisoalloxazine chloride oxidizing NADH at different pHs

| pH | TON | TOF (min$^{-1}$) |
|---|---|---|
| 4 | 36.01 | 3.60 |
| 5 | 38.91 | 3.89 |
| 6 | 53.06 | 5.31 |
| 7 | 95.18 | 9.52 |
| 8 | 72.67 | 7.27 |
| 9 | 49.84 | 4.98 |
| 10 | 19.29 | 1.93 |

Example 9: 7-Trifluoromethyl-1,10-Ethyleneisoalloxazine Chloride Oxidizing NADH at Different Temperatures In a 50 mM potassium phosphate buffer of pH 7, the initial concentration of NADH was 0.2 mM, the concentration of 7-trifluoromethyl 1,10-ethyleneisoalloxazine chloride was 0.5 µM, the reaction solution was connected with the outside air, after being reacted at 30° C., 40° C., 50° C., 60° C., and 70° C. respectively for 10 minutes, the light absorption value at 340 nm was detected, the concentrations of NADH and NAD+ were calculated, TON and TOF at different temperatures were calculated, and the results are shown in Table 6, when T<40° C., changes of TON and TOF with temperature was not large, when T>40° C., TON and TOF were reduced with increase in temperature, the reason is that solubility of air in water is reduced with increase in temperature.

TABLE 6

TON and TOF of 7-trifluoromethyl-1,10-ethyleneisoalloxazine chloride oxidizing NADH at different pHs

| T (° C.) | TON | TOF (min$^{-1}$) |
|---|---|---|
| 30 | 96.78 | 9.68 |
| 40 | 96.14 | 9.61 |
| 50 | 56.27 | 5.63 |
| 60 | 48.23 | 4.82 |
| 70 | 42.77 | 4.28 |

Example 10: Substituted Derivative of 1,10-Ethyleneisoalloxazine Chloride Oxidizing NADH to NAD$^+$ At 30° C., in a 50 mM potassium phosphate buffer of pH 7, the initial concentration of NADH was 0.2 mM, the concentrations of 7-trifluoromethyl-3-methyl-1,10-ethyleneisoalloxazine chloride (Compound A), 7-methyl-1,10-ethyleneisoalloxazine chloride (Compound B), 8-methyl-1,10-ethyleneisoalloxazine chloride (Compound C), 7,8-dimethyl-1,10-ethyleneisoalloxazine chloride (Compound D), 3-benzyl-1,10-ethyleneisoalloxazine chloride (Compound E) were 0.5 µM, the reaction solution was connected with the outside air, after being reacted for 10 minutes, the light absorption value at 340 nm was detected, the concentrations of NADH and NAD+ were calculated, TON and TOF at different temperatures were calculated, and the results are show in Table 7.

TABLE 7

TON and TOF of several bridged flavins catalytically oxidizing NADH

| Compound | TON | TOF (min$^{-1}$) |
|---|---|---|
| A | 89.34 | 8.93 |
| B | 70.53 | 7.05 |
| C | 69.98 | 7.00 |
| D | 56.88 | 5.69 |
| E | 75.27 | 7.53 |

Example 11: 7-Trifluoromethyl-1,10-Ethyleneisoalloxazine Chloride as a Catalyst for Regenerating NAD$^+$ Coupled with Horse Liver Alcohol Dehydrogenase Catalyzing Lactonization of 1,4-Butandioloxidize to γ-Butyrolactone At 30° C., in a 1 mL 50 mM potassium phosphate buffer (pH8) of 1,4-butanediol 20 mM, NAD$^+$ 0.1 mM, 7-trifluoromethyl-1,10-ethyleneisoalloxazine 0.05 mM, catalase 50 U/mL, and horse liver alcohol dehydrogenase 20 U/mL, the reaction solution was connected with the outside air. 200 µL reaction solution were taken out respectively at 1 h, 2 h, 4 h, 8 h of reaction, and 200 µL ethyl acetate was added for extraction, the reaction process was detected by gas chromatography, and the results are shown in Table 8:

TABLE 8

Conversion rate with reaction time of 7-trifluoromethyl-1,10-ethyleneisoalloxazine chloride coupled with horse liver alcohol dehydrogenase catalyzing 1,4-butanediol

| time (h) | conversion rate (%) |
|---|---|
| 1 | 38 |
| 2 | 71.18 |
| 4 | 93 |
| 8 | 100 |

Example 12:
7-Trifluoromethyl-1,10-Ethyleneisoalloxazine Chloride as a Catalyst for Regenerating $NAD^+$ Coupled with Horse Liver Alcohol Dehydrogenase Catalyzing Oxidization of Cyclohexanol to Cyclohexanone At 30° C., in a 1 mL 50 mM potassium phosphate buffer (pH8) of cyclohexanol 20 mM, $NAD^+$ 0.1 mM, 7-trifluoromethyl-1,10-ethyleneisoalloxazine 0.05 mM, catalase 50 U/mL, horse liver alcohol dehydrogenase 20 U/mL, the reaction solution was connected with the outside air connect. 200 μL reaction solution were taken out respectively at 1 h, 2 h, 4 h, 8 h, 12 h, 24 h of the reaction, 200 μL ethyl acetate was added for extraction, the reaction process was detected by gas chromatography, and the results are shown in Table 9:

TABLE 9

Conversion rate with reaction time of 7-trifluoromethyl-1,10-ethyleneisoalloxazine chloride coupled with horse liver alcohol dehydrogenase catalyzing cyclohexanol

| time (h) | conversion rate (%) |
|---|---|
| 1 | 31 |
| 2 | 39.23 |
| 4 | 51.36 |
| 8 | 62.3 |
| 24 | 90.72 |

Example 13:
7-Trifluoromethyl-1,10-Ethyleneisoalloxazine Chloride as a Catalyst for Regenerating $NAD^+$ Coupled with Horse Liver Alcohol Dehydrogenase Catalyzing Oxidization and Lactonization of 3-Methyl-1,5-Pentanediol to 3-Methylvalerolactone At 30° C., in a 1 mL 50 mM potassium phosphate buffer (pH8) of 3-methyl-1,5-pentanediol 20 mM, $NAD^+$ 0.1 mM, 7-trifluoromethyl-1,10-ethyleneisoalloxazine 0.05 mM, catalase 50 U/mL, horse liver alcohol dehydrogenase 20 U/mL, the reaction solution was connected with the outside air. 200 μL reaction solution were taken out respectively at 1 h, 2 h, 4 h, 8 h, 12 h, 24 h of the reaction, 200 μL ethyl acetate was added for extraction, the reaction process was detected by gas chromatography, and the results are shown in Table 10.

TABLE 10

Conversion rate with reaction time of 7-trifluoromethyl-1,10-ethyleneisoalloxazine chloride coupled with horse liver alcohol dehydrogenase catalyzing 3-methyl-1,5-pentanediol

| time (h) | conversion rate (%) |
|---|---|
| 1 | 59.83 |
| 2 | 71.18 |
| 4 | 82.76 |
| 8 | 93.77 |
| 12 | 98.64 |
| 24 | 100 |

Example 14:
7-Trifluoromethyl-1,10-Ethyleneisoalloxazine Chloride as a Catalyst for Regeneration $NAD^+$ Coupled with Glucose Dehydrogenase Catalytically Oxidizing Glucose to Gluconic Acid At 30° C., in a 10 mL reaction system of glucose 25 mM, $NAD^+$ 0.5 mM, 7-trifluoromethyl-1,10-ethyleneisoalloxazine 0.5 mM, NaCl 50 mM, catalase 50 U/mL, glucose dehydrogenase 120 U/mol (glucose), the reaction solution was connected with the outside air. 200 μL reaction solution were taken out respectively at 1 h, 2 h, 4 h, 6 h of the reaction, 800 μL water was added for dilution, the reaction process was detected by liquid chromatography, and the results are shown in Table 11.

TABLE 11

Conversion rate with reaction time of 7-trifluoromethyl-1,10-ethyleneisoalloxazine chloride coupled with glucose dehydrogenase catalyzing glucose

| time (h) | conversion rate (%) |
|---|---|
| 1 | 38.1 |
| 2 | 55.0 |
| 4 | 89.6 |
| 6 | 100 |

Example 15:
7-Trifluoromethyl-1,10-Ethyleneisoalloxazine Chloride as a Catalyst for Regenerating $NAD^+$ Coupled with Glucose Dehydrogenase Catalytically Oxidizing Xylose to Xylonic Acid At 30° C., in a 10 mL reaction system of xylose 25 mM, $NAD^+$ 0.5 mM, 7-trifluoromethyl-1,10-ethyleneisoalloxazine 0.5 mM, NaCl 50 mM, catalase 50 U/mL, glucose dehydrogenase 120 U/mol (xylose), the reaction solution was connected with the outside air. 200 μL reaction solution were taken out respectively at 1 h, 2 h, 4 h, 6 h, 12 h, 24 h of the reaction, 800 μL water was added for dilution, the reaction process was detected by liquid chromatography, and the results are shown in Table 12.

TABLE 12

Conversion rate with reaction time of 7-trifluoromethyl-1,10-ethyleneisoalloxazine chloride coupled with glucose dehydrogenase catalyzing xylose

| time (h) | conversion rate (%) |
|---|---|
| 1 | 17.5 |
| 2 | 32.3 |

TABLE 12-continued

Conversion rate with reaction time of 7-trifluoromethyl-1,10-ethyleneisoalloxazine chloride coupled with glucose dehydrogenase catalyzing xylose

| time (h) | conversion rate (%) |
|---|---|
| 4 | 52.1 |
| 6 | 65.9 |
| 8 | 76.8 |
| 12 | 82.9 |
| 24 | 100 |

Example 16:
7-Trifluoromethyl-1,10-Ethyleneisoalloxazine Chloride as a Catalyst for Regenerating NAD$^+$ Coupled with Glycerol Dehydrogenase Catalytically Oxidizing Glycerol to 1,3-Dihydroxyacetone At 30° C., in 10 mL reaction system (potassium phosphate buffer of 50 mM and pH 10) of glycerol 25 mM, NAD$^+$ 0.5 mM, 7-trifluoromethyl-1,10-ethyleneisoalloxazine chloride 0.5 mM, atalase 50 U/mL, glycerol dehydrogenase 120 U/mol, the reaction solution was connected with the outside air. 200 µL reaction solution were taken out respectively at 1 h, 2 h, 4 h, 8 h, 12 h, 24 h of the reaction, 800 µL of water was added for dilution, the reaction process detected by liquid chromatography, and the results are shown in Table 13.

TABLE 13

Conversion rate with reaction time of 7-trifluoromethyl-1,10-ethyleneisoalloxazine chloride coupled with glycerol dehydrogenase catalyzing glycerol

| time (h) | conversion rate (%) |
|---|---|
| 1 | 235 |
| 2 | 56.3 |
| 4 | 51.7 |
| 8 | 72.6 |
| 12 | 86.5 |
| 24 | 100 |

What is claimed is:

1. A method for regenerating chemically an oxidized coenzyme NAD(P)$^+$, characterized in that, under an oxygen or air atmosphere condition, adding a catalytic amount of a bridged flavin, and oxidizing NAD(P)H to obtain NAD(P)$^+$, wherein the bridged flavin has a formula as follow:

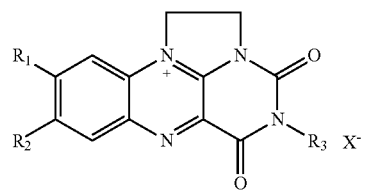

wherein, $R_1$ and $R_2$ are independently selected from a group consisting of hydrogen, methyl, trifluoromethyl, methoxyl, halogen atom, nitro and amino; $R_3$ is selected from a group consisting of hydrogen, C1-C5 alkyl, phenyl and benzyl; $X^-$ is selected from a group consisting of halide ion, nitrate radical and trifluoromethanesulfonic acid radical.

2. The method according to claim 1, characterized in that, the bridged flavin is 7-trifluoromethyl-1,10-ethyleneisoalloxazine chloride (Compound I), 8-chloro-1,10-ethyleneisoalloxazine chloride (Compound II), or 1,10-ethyleneisoalloxazine chloride (Compound III) having chemical structures shown as

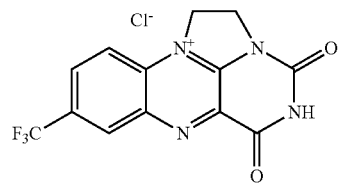

(I)

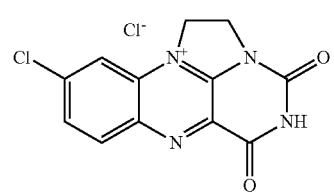

(II)

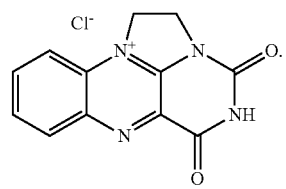

(III)

3. The method according to claim 1, characterized in that, the mole number of the catalytic amount of the bridged flavin is 0.1-5% of the mole number of the NAD(P)H.

4. The method according to claim 1, characterized in that, the condition for oxidizing NAD(P)H into NAD(P)$^+$ is in a pH 4-10 and at a temperature 30-70° C.

5. The method according to claim 1, characterized in that, the bridged Flavin is coupled with an oxidation reaction catalyzed by a NAD(P)$^+$-dependent oxidoreductase, forming a regeneration circulation system of the coenzyme NAD(P)$^+$.

6. The method according to claim 5, characterized in that, the NAD(P)$^+$-dependent oxidoreductase is one or more enzymes selected from a group consisting of EC1.1.1.X, EC1.2.1.X, EC1.3.1.X, EC1.4.1.X, EC1.5.1.X, EC1.6.1.X, EC1.7.1.X, EC1.8.1.X, EC1.10.1.X, EC1.12.1.X, EC1.13.1.X, EC1.16.1.X, EC1.17.1.X, EC1.18.1.X, EC1.20.1.X and EC1.22.1.X.

7. The method according to claim 6, characterized in that, the NAD(P)$^+$-dependent oxidoreductase is horse liver alcohol dehydrogenase (EC1.1.1.1), glucose dehydrogenase (EC1.1.1.47) or glycerol dehydrogenase (EC1.1.1.6).

8. A process for an oxidation reaction by using a NAD(P)$^+$-dependent oxidoreductase as a catalyst, characterized in that, using a bridged flavin as a NAD(P)$^+$ regeneration catalyst, under oxygen or air atmosphere condition, oxidizing NAD(P)H into NAD(P)$^+$, forming a regeneration circulation system of coenzyme NAD(P)$^+$; wherein the bridged flavin has a formula as follow:

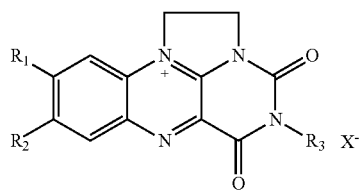

wherein, $R_1$ and $R_2$ are independently selected from a group consisting of hydrogen, methyl, trifluoromethyl, methoxyl, halogen atom, nitro and amino; $R_3$ is selected from a group consisting of hydrogen, C1-C5 alkyl, phenyl and benzyl; $X^-$ is selected from a group consisting of halide ion, nitrate radical and trifluoromethanesulfonic acid radical.

9. The process according to claim 8, characterized in that, the bridged flavin is 7-trifluoromethyl-1,10-ethyleneisoalloxazine chloride (Compound I), 8-chloro-1,10-ethyleneisoalloxazine chloride (Compound II), or 1,10-ethyleneisoalloxazine chloride (Compound II) having chemical structures shown as

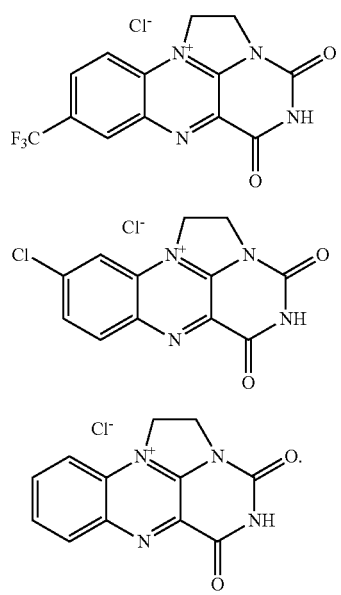

10. The process according to claim 8, characterized in that, the mole number catalyzed by the bridged flavin is 0.1-5% of the mole number of a substrate catalyzed by an enzyme.

11. The process according to claim 8, characterized in that, the condition for oxidizing NAD(P)H into NAD(P)$^+$ is in pH 4-10 and at temperature 30-70° C.

12. The process according to claim 8, characterized in that, the NAD(P)$^+$-dependent oxidoreductase is one or more enzymes selected from a group consisting of EC1.1.1.X, EC1.2.1.X, EC1.3.1.X, EC1.4.1.X, EC1.5.1.X, EC1.6.1.X, EC1.7.1.X, EC1.8.1.X, EC1.10.1.X, EC1.12.1.X, EC1.13.1.X, EC1.16.1.X, EC1.17.1.X, EC1.18.1.X, EC1.20.1.X and EC1.22.1.X.

13. The process according to claim 12, characterized in that, the NAD(P)$^+$-dependent oxidoreductase is horse liver alcohol dehydrogenase (EC1.1.1.1), glucose dehydrogenase (EC1.1.1.47) or glycerol dehydrogenase (EC1.1.1.6).

14. A method for using a bridged flavin as a catalyst for oxidizing NAD(P)H into NAD(P)$^+$; wherein the bridged flavin has a formula as follow:

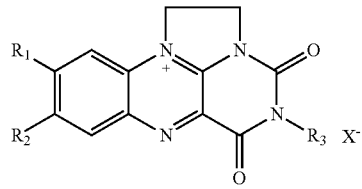

wherein, $R_1$ and $R_2$ are independently selected from a group consisting of hydrogen, methyl, trifluoromethyl, methoxyl, halogen atom, nitro and amino; $R_3$ is selected from a group consisting of hydrogen, C1-C5 alkyl, phenyl and benzyl; $X^-$ is selected from a group consisting of halide ion, nitrate radical and trifluoromethanesulfonic acid radical.

15. The method according to claim 14, characterized in that, the bridged flavin is 7-trifluoromethyl-1,10-ethyleneisoalloxazine chloride (Compound I), 8-chloro-1,10-ethyleneisoalloxazine chloride (Compound II), or 1,10-ethyleneisoalloxazine chloride (Compound III) having chemical structures shown as

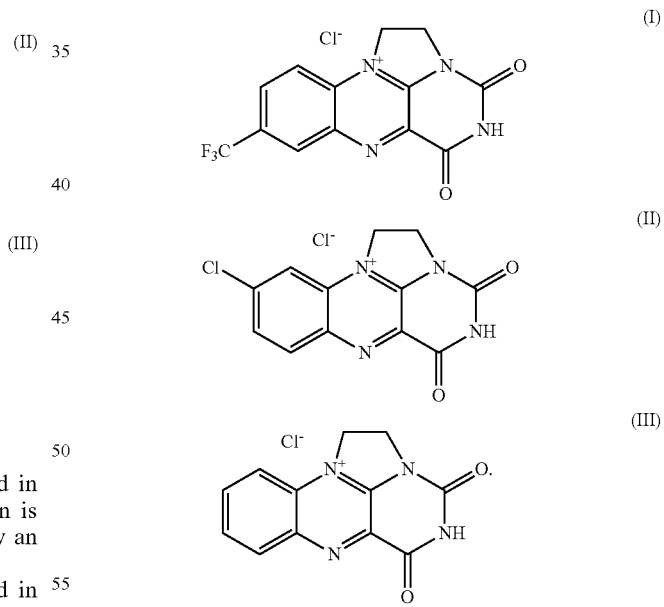

16. The method according to claim 14, characterized in that, the mole number catalyzed by the bridged flavin is 0.1-5% of the mole number of NAD(P)H.

17. The method according to claim 14, characterized in that, the condition for oxidizing NAD(P)H into NAD(P)$^+$ is in pH 4-10 and at temperature 30-70° C.

* * * * *